US00PP33102P3

(12) United States Plant Patent
Klemm et al.

(10) Patent No.: US PP33,102 P3
(45) Date of Patent: May 25, 2021

(54) ***CALIBRACHOA* PLANT NAMED 'KLECA18504'**

(50) Latin Name: ***Calibrachoa* sp.**
Varietal Denomination: KLECA18504

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,013

(22) Filed: May 10, 2020

(65) Prior Publication Data

US 2020/0383259 P1 Dec. 3, 2020

Related U.S. Application Data

(60) Provisional application No. 62/921,069, filed on May 29, 2019.

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ... A01H 5/02; A01H 5/12; A01H 5/00; A01H 6/82; A01H 6/821; A01H 6/14
See application file for complete search history.

(56) References Cited

PUBLICATIONS

Ball Seed Minifamous Neo Violet Ice, retrieved on Oct. 19, 2020, retrieved from the Internet at https://www.ballseed.com/PlantInfo/?phid=066007160004397, one page. (Year: 2020).*
Ball Seed Highlights from 2019 California Spring Trials, retrieved on Oct. 19, 2020, retrieved from the Internet at file:///C:/Users/jhwu/Downloads/19006_BSC_NV_CAST_book_LR.pdf, 3 intro pages, 19. (Year: 2019).*
Wright Floriculture's Finest Plant Varieties Coming Soon to California Spring Trials 2019, retrieved from the Internet at https://www.greenhousegrower.com/crops/floricultures-finest-plant-varieties-coming-soon-to-california-spring-trials-2019/, 8 pp. (Year: 2019).*

* cited by examiner

*Primary Examiner* — June Hwu
(74) *Attorney, Agent, or Firm* — Weatherly IP Solutions, LLC; Barbara Campbell

(57) ABSTRACT

A new *Calibrachoa* plant designated 'KLECA18504' particularly distinguished by violet flowers, is disclosed.

1 Drawing Sheet

Genus and species: *Calibrachoa* sp.
Variety denomination: 'KLECA18504'.

BACKGROUND OF THE NEW PLANT

The present invention comprises a new and distinct variety of *Calibrachoa*, botanically known as *Calibrachoa* sp., and hereinafter referred to by the variety name 'KLECA18504'. 'KLECA18504' originated from a controlled cross between the proprietary female *Calibrachoa* parent 'CA-2015-6479', (unpatented) and the proprietary male *Calibrachoa* 'CA-2015-6488', (unpatented) in Stuttgart, Germany in August 2015.

'KLECA18504' has been found to reproduce true to type in successive generations of asexual propagation in Stuttgart, Germany via vegetative stem cuttings.

SUMMARY

The following are the most outstanding and distinguishing characteristics of 'KLECA18504' when grown under normal horticultural practices in Stuttgart, Germany.

1. Light violet flowers with a dark violet eye; and
2. A semi-trailing habit.

DESCRIPTION OF THE PHOTOGRAPH

This new *Calibrachoa* plant is illustrated by the accompanying photograph of a plant grown outdoors in Stuttgart, Germany. The photograph shows the whole plant, unless otherwise noted, including the flowers and foliage and buds. The colors shown are as true as can be reasonably obtained by conventional photographic procedures. The photograph is of a whole plant photo of 'KLECA18504', taken at 3-months-old in June 2018.

DESCRIPTION OF THE NEW VARIETY

The following detailed descriptions set forth the distinctive characteristics of 'KLECA18504'. The data which define these characteristics were collected from asexual reproductions carried out in Stuttgart, Germany. Data was collected on plants grown 18 weeks since potting in a greenhouse with no pinching or growth regulators. Color references are to The R.H.S. Colour Chart of The Royal Horticultural Society of London (R.H.S.), 5$^{th}$ edition (2007).

Classification:
*Family*.—Solanaceae.
*Botanical*.—*Calibrachoa* sp.
*Designation*.—'KLECA18504'.

Parentage:
*Female parent*.—'CA-2015-6479' (unpatented).
*Male parent*.—'CA-2015-6488' (unpatented).
Plant:
*Life cycle*.—Annual.
*Form*.—Short-lived subshrub.
*Habit*.—Spreading, trailing.
*Height* (*from soil line to top of foliage*).—8 cm.
*Spread*.—38 cm.
*Propagation*.—Vegetative.
*Type cuttings*.—Tip cuttings.
*Time to produce a rooted cutting*.—3 weeks.
*Disease and pest resistance/susceptibility*.—To date, plants of 'KLECA18504' have not been observed to be resistant or susceptible to pathogens and pests common to *Calibrachoa* plants.
Stems:
*Stem color*.—RHS 144C.
*Pubescence*.—Present.
*Pubescence color*.—RHS 157B.
*Stem diameter*.—0.1 cm.
*Stem length*.—From soil line to first node: 2.0 cm. Total length: 38 cm.
*Internode length*.—2.7 cm.
Foliage:
*Arrangement*.—Opposite.
*Shape*.—Elliptic.
*Apex*.—Broadly acute.
*Base*.—Attenuate.
*Margin*.—Entire.
*Surface*.—Moderately glandular pubescent.
*Surface pubescence*.—Present.
*Pubescence color*.—RHS 157B.
*Venation*.—Arcuate.
*Venation color*.—Upper surface: RHS 144C. Lower surface: RHS 144B.
*Length*.—4.0 cm.
*Width*.—1.8 cm.
*Color*.—Upper surface: RHS 137B. Lower surface: RHS 138B.
*Fragrance*.—Absent.
Inflorescence:
*Flowering habit*.—Single flowers.
*Flower type*.—Determinate inflorescence.
*Flowering requirements*.—A minimum of light sun is required.
*Duration of flowers*.—6 days.
*Shape*.—Funnel form.
*Lobing of the flower*.—Medium.
*Conspicuousness of the veins of the flower, inner and outer surfaces*.—Strong.
*Fragrance*.—Absent.
*Flower depth*.—1.8 cm.
*Flower tube length*.—1.5 cm.
*Flower tube diameter*.—0.8 cm.
*Flower diameter*.—3.6 cm.
*Calyx*.—Funnel shaped, salverform.
Inflorescence bud:
*Surface*.—Smooth.
*Length*.—2.1 cm.
*Diameter*.—0.5 cm.
*Shape*.—Elliptic.
*Color*.—RHS 1C (throat) and RHS 155C (limbs).
Peduncles:
*Length*.—2.2 cm.
*Diameter*.—0.1 cm.
*Color*.—RHS 144C.
*Texture*.—Densely glandular pubescent.
*Anthocyanin color*.—Absent.
Sepals:
*Shape*.—Lanceolate.
*Apex*.—Narrowly acute.
*Margin*.—Entire.
*Length*.—1.1 cm.
*Diameter*.—0.2 cm.
*Sepal color*.—Upper surface: RHS 137B. Lower surface: RHS 137D.
Petals:
*Shape*.—Obcordate.
*Length*.—1.9 cm.
*Apex*.—Truncate.
*Margin*.—Entire.
*Base*.—Fused in the tube.
*Texture, upper surface*.—Glabrous.
*Texture, lower surface*.—Glandular pubescent, dense along venation.
*Lobe length*.—1.9 cm.
*Lobe width*.—1.9 cm.
*Color*.—Lobe color: Upper surface: RHS 85D with an eye color of RHS 86A and the transition area as bring medium in size. Lower surface: RHS 84D. Corolla tube color: Inner: RHS 150D. Outer: RHS 3C. Immature and fading color: No different from the mature color.
*Fragrance*.—Absent.
Reproductive organs:
*Stamen number*.—5.
*Anther color*.—RHS 3C.
*Filament color*.—RHS 150C.
*Pollen color*.—RHS 8B.
*Placenta arrangement*.—Ovate.
*Pistil number*.—1.
*Pistil length*.—0.7 cm.
*Stigma color*.—RHS 144C.
*Style length*.—0.8 cm.
*Style color*.—RHS 144C.
Fruit and seed set: No fruit or seed set observed.

COMPARISON OF 'KLECA18504' WITH PARENTAL LINES AND KNOWN VARIETY

'KLECA18504' is distinguished from the parental lines as follows. Whereas 'KLECA18504' has light violet flowers with a dark violet eye, the female parent 'CA-2015-6479' has dark violet flowers with an eye and the male parent 'CA-2015-6488' has blue flowers with an eye.

'KLECA18504' can be compared to the commercial *Calibrachoa* variety 'Hula Lavender', (patent status unknown) as follows. 'KLECA18504' flowers earlier than 'Hula Lavender'. Additionally, 'KLECA18504' has a semi-trailing habit with light violet flowers with a dark violet eye, whereas 'Hula Lavender' has a semi-upright habit and light lavender flowers with a lavender eye.

We claim:

1. A new and distinct variety of *Calibrachoa* plant designated 'KLECA18504' as illustrated and described herein.

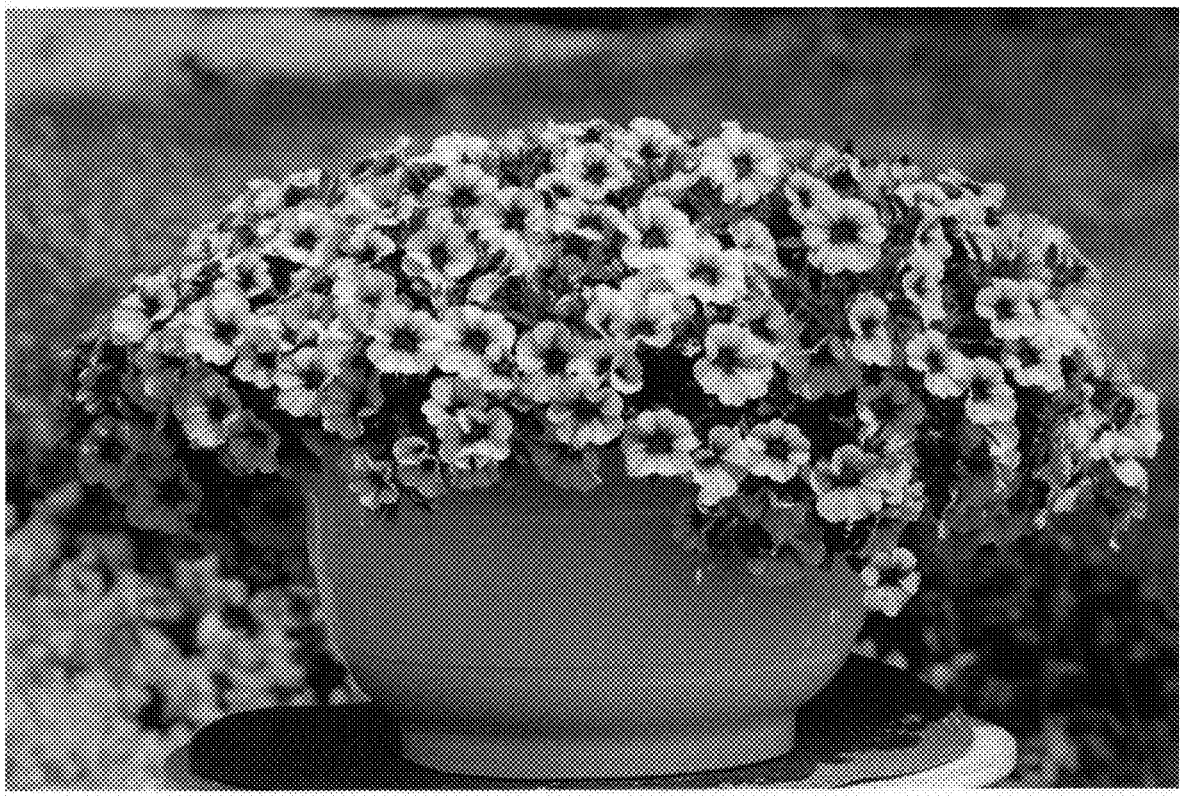

* * * * *